United States Patent [19]

Lienhard

[11] Patent Number: 5,267,569
[45] Date of Patent: Dec. 7, 1993

[54] BLOOD FLOW MEASURING APPARATUS

[75] Inventor: Brigit Lienhard, Zurich, Switzerland

[73] Assignees: Hans Baer; Eduard Hirsbrunner, both of Zurich, Switzerland

[21] Appl. No.: 766,274

[22] Filed: Sep. 27, 1991

[51] Int. Cl.$^5$ .................... A61B 5/026; A61B 5/05
[52] U.S. Cl. .................... 128/691; 128/734; 324/71.1
[58] Field of Search .................... 128/691–693, 128/723, 734, 735, 642; 324/71.1; 73/23.2, 31.05

[56] References Cited

U.S. PATENT DOCUMENTS

| | | | |
|---|---|---|---|
| 4,951,682 | 8/1990 | Petre | 128/713 |
| 5,081,990 | 1/1992 | Deletis | 128/642 |
| 5,092,339 | 3/1992 | Geddes et al. | 128/692 |
| 5,121,750 | 6/1992 | Katims | 128/734 |

FOREIGN PATENT DOCUMENTS 3330358 3/1985 Fed. Rep. of Germany .
2146436 4/1985 United Kingdom .

OTHER PUBLICATIONS

*IEEE Transactions on Biomedical Engineering*, vol. BME-28, No. 3, Mar. 1981, pp. 265-270, New York, N.Y., J. B. Myklebust et al.: "A Combination Isothermal-Hydrogen Clearance System for the Measurement of Local Tissue Flow".

*Physics in Medicine & Biology*, vol. 34, No. 10, Oct. 1989, pp. 1413-1428, Woodbury, N.Y., D. K. Harrison et al.: "Local hydrogen clearance as a method for the measurement of capillary blood flow".

"Measurement of Local Blood Flow With Hydrogen Gas", by Knut Aukland et al., in Circulation Research vol. XIV, 1964, pp. 164 et seq.

"H2 Clearance Measurement of Blood Flow: A Review of Technique and Polarographic Principles", by Wise Young, Ph.D., M.D., Stroke, vol. 11, No. 5, Sep.-Oct. 1980 pp. 552 to 564.

Product Manual about isolation amplifier, Jul. 1984 Product Data Manual of Burr-Baun Corporation.

"Datenerfassungs-Chip ersetzt 30 Standard-ICs" by G. McGlinchey et al., "Electronik", 13/Jun. 22, 1990, pp. 90 to 93.

"Theoretical Analysis of Diffusion Effects", by Pierce et al., Stroke, vol. 13, No. 3, 1982, pp. 347-355.

"New Methods to Evaluate Hydrogen Clearance With Locally Generated Hydrogen" by R. Wodick in Arsneim. Forsch. (Drug Res.) 25, Nr. 6 (1975) Rundschau, pp. 978 to 979.

"Theoretical Analysis Based on Computer Sinulation for Hydrogen Clearance Method Applying Electrolysis", by Makoto Umemori of Nippon Medical School, four pages.

"Quantitative Evaluation of Continuous Measurement of Hydrogen by Locally Applied Hydrogen", by Uwe Grossmann et al, in 9th Europ. Conf. Microcirculation, Antwerp 1976, Bibl. anat., No. 16, pp. 339 to 341 (Karger, Basel 1977).

"Measurements of Microflow by Local Hydrogen Clearance", by E. Leniger-Follert et al., in Arsneim. Forsch. (Drug Res.) 25, Nr. 6 (1975), Rundschau, pp. 983 to 985.

"Molecular Diffusion; Fick's Law", in the book Fundamental University Physics, vol. II, Fields and Waves, Addison-Wesley Publishing Company, Inc., Second Printing 1970, Chapter 24.2, pp. 934 to 941.

*Primary Examiner*—Lee S. Cohen
*Assistant Examiner*—Kevin Pontius
*Attorney, Agent, or Firm*—Sandler Greenblum & Bernstein

[57] ABSTRACT

The blood flow measuring apparatus comprises at least three electrodes, namely, a measuring electrode, reference electrode and an active neutral electrode, which are implanted at a predetermined tissue region. The signals of the measuring electrode and the reference electrode are delivered by input lines to a current and voltage isolated differential amplifier, the output of which is connected with a central unit controlling further instruments. What is important for the measuring accuracy of the blood flow measuring apparatus is an opposite feedback of external spurious fields which couple-in spurious potentials into the tissue and the shields of the input lines of the measuring electrode, reference electrode and neutral electrode. Further probes can be provided as an aid for the central unit.

8 Claims, 2 Drawing Sheets

Fig. 1

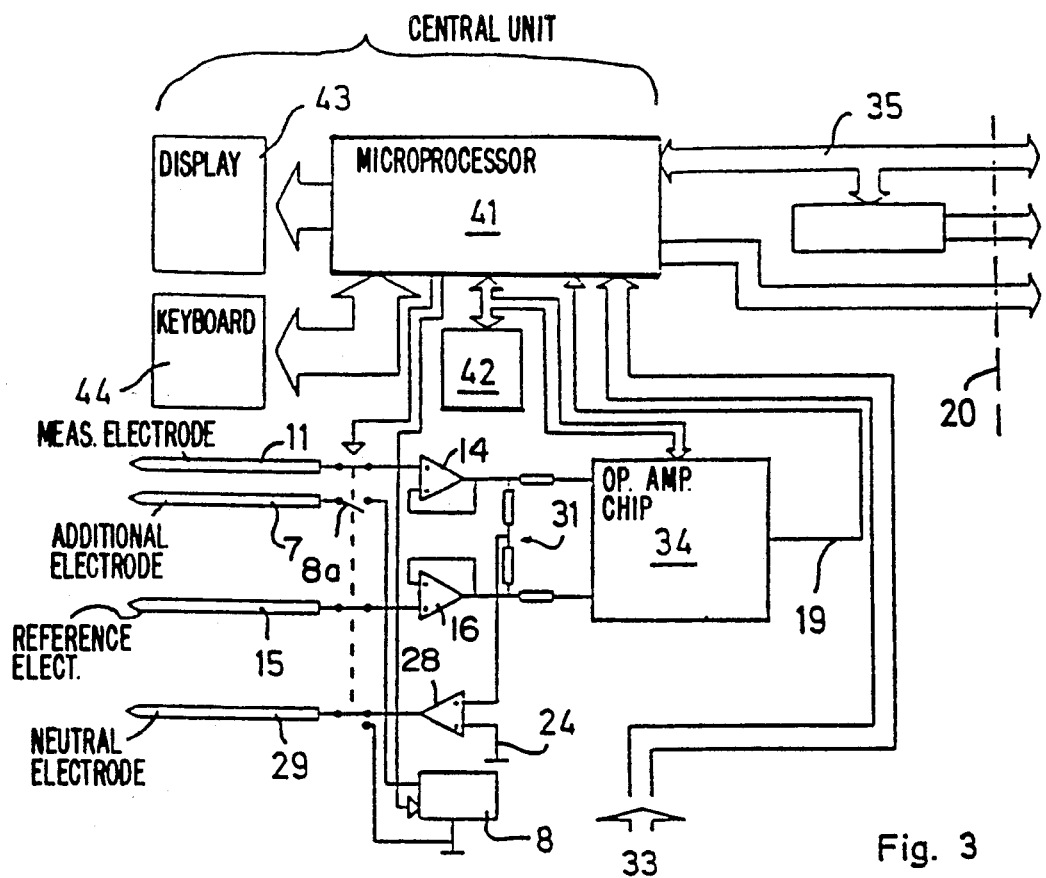
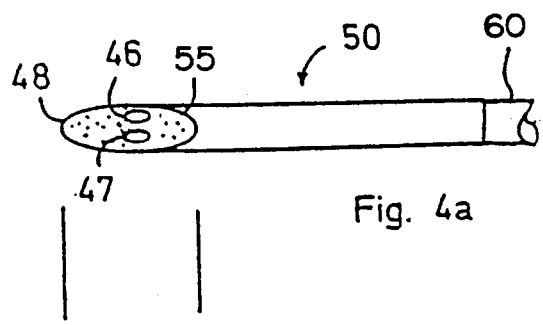
Fig. 4a
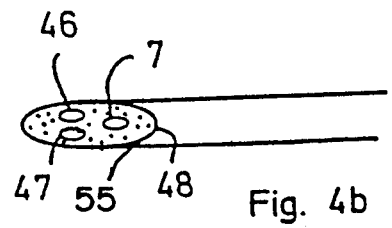
Fig. 4b
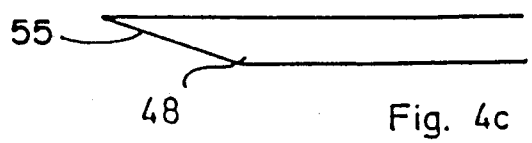
Fig. 4c

BLOOD FLOW MEASURING APPARATUS

BACKGROUND OF THE INVENTION

1. Field of the Invention

The present invention relates to a new and improved blood flow measuring apparatus operating according to the $H_2$ clearance measurement technique which comprises a measuring electrode, a reference electrode and a neutral electrode, and further contains an operational amplifier and a signal display device.

2. Discussion of the Background and Material Information

The blood flow through human and animal tissue is an important indicator both for diagnostics and also for the control of the progress and success of therapy or a surgical invasive procedure as well as for the trial and observation of the efficacacy of medication. Therefore numerous publications exist reporting experiences which have been had with measuring apparatuses for this purpose.

According to a prior art method for the determination of the blood flow through tissues a suitable radioactive material having a short half-life time is implanted in the tissue to be investigated. The decomposition products of this radioactive material preferably exhibit a still shorter half-life time and as a gaseous substance are dissolvable in blood. During the radioactive decomposition of the implanted material and the decomposition products there is produced radiation, the intensity of which can be measured with suitable instruments. The behavior of this intensity, in other words, the change of this behavior as a function of time allows for the quantitative determination of the decomposition products which have been washed out of the tissue by the blood flow, and thus, also enables determining the blood flow through the tissue.

The disadvantages of this method should be readily apparent. Very few radioactive materials are known which possess the previously considered properties and which can be produced with the required purity. The implantation of the radioactive material requires surgery and can not be carried out at every tissue or organ. Certain radioactive decomposition products tend to concentrate in certain tissues or organs and can cause protracted damage thereto. The instruments for measuring the intensity of the radioactive radiation of the implantation and the decomposition products detect a relatively large tissue volume, explaining why it is not possible to determined the blood flow through smaller tissue regions. Additionally, such instruments can only be used by trained personnel, are technically very complicated and therefore quite expensive.

According to a different prior art method, usually referred to as the $H_2$ clearance measurement technique or method, the blood of the test subject or person is enriched with hydrogen and used as electrolyte forming a galvanic element in conjunction with two electrodes inserted into the tissue to be examined. The electrical potential of this galvanic element is governed, among other things, by the concentration of the hydrogen in the blood. When performing such $H_2$ clearance measurement the hydrogen is introduced through the respiratory air or by injection into the blood. As soon as the electrical potential between the two electrodes has reached a certain threshold value there is interrupted the infeed of hydrogen and there is observed the decrease of the electrical potential as a function of time. The steepness or slope of the curve of this function constitutes a measure of the flow of blood through the tissue, during which the blood enriched with hydrogen is removed and replaced by hydrogen-free blood.

The theoretical basis for this $H_2$ clearance measurement method, in particular the computation of the electrical potential of the electrodes as a function of the hydrogen-ion concentration using the Nernst equation and the determination of the flow of blood through a tissue volume by virtue of the decrease in the concentration of the hydrogen in the blood by means of the Fick principle or law, have been extensively described, for example, by Knut Aukland et al in Circulation Research, Volume XIV, 1964, pages 164 et seq. When performing this $H_2$ clearance measurement method no implantation or complicated equipment is required. Additionally, this $H_2$ clearance measurement method allows for repeated determinations of the blood flow through a tissue with altered conditions, and the comparatively small electrodes enable determining the blood flow through relatively small tissue volumes.

Notwithstanding these advantages and even though the determination of the flow of blood through tissues by means of an inert gas or hydrogen has been known for at least forty years and has been discussed in numerous publications, the practical application of this method has previously been essentially confined to experiments with animals and there is only known the measuring of the rate of blood flow which has been performed on the tip of the small finger of a human. The reasons for this are quite simple. With the apparatuses previously employed for the performance of the aforedescribed method there only could be accomplished measurements, which could be evaluated and were reproducible, if the current intensity between the electrodes, and thus, also in the blood and at the tissue to be investigated amounted to at least $1 \cdot 10^{-6}$ Amp., a value which is physiologically questionable or even, in fact, impermissible for certain tissues.

Such a measuring apparatus has been described, for example, in the article: "H$_2$ Clearance Measurement of Blood Flow: A Review of Technique and Polarographic Principles", authored by Wise Young, Ph.D., M.D.; in the publication "Stroke", Vol. 11, No. 5, September-October 1980, pages 552 to 564.

SUMMARY OF THE INVENTION

Therefore, with the foregoing in mind, it is a primary object of the present invention to provide an improved blood flow measuring apparatus which is capable of reproducibly carrying out the $H_2$ clearance measurement method or technique in a manner not afflicted with the aforementioned drawbacks and shortcomings of the prior art.

Another and more specific important object of the present invention is to provide an improved blood flow measuring apparatus which is capable of reproducibly carrying out the $H_2$ clearance measurement method or technique for determining the blood flow through tissues or organs with physiologically safe current intensities.

Yet a further significant object of the present invention is concerned with the provision of a blood flow measuring apparatus for the accurate performance of the $H_2$ clearance measurement method or technique, which is relatively simple to use, operationally reliable and also can be operated by trained attendants or auxiliary personnel or the like.

Still a further noteworthy object of the present invention is directed to the provision of an improved substantially needle-shaped measuring probe for use with a blood flow measuring apparatus operating according to the $H_2$ clearance measurement technique.

Now in order to implement these and still further objects of the present invention, which will become more readily apparent as the description proceeds, the blood flow measuring apparatus of the present development is manifested, among other things, by the features that the measuring electrode and the reference electrode are formed of metals, the natural or inherent chemical potential of which lie close to one another. The measuring electrode and the reference electrode are connected by input lines to the inputs of an operational amplifier in order to form the difference of their potentials. The measuring electrode, the reference electrode and the neutral electrode and their input lines possess a shield or screen against external spurious fields. The shields or screens of at least the measuring electrode and the reference electrode and the input lines of such measuring electrode and reference electrode are connected by the non-inverting or positive input of a voltage amplifying and inverting circuit with the neutral electrode in order to produce a potential in the tissue which is opposite to or out of phase with inductive or capacitive coupled-in potential fluctuations. Moreover, the inverting or negative input of this voltage amplifying and inverting circuit are connected with a voltage divider connected between the input lines of the measuring electrode and reference electrode in order to form an average or mean value of the potentials of the measuring electrode and reference electrode.

By means of the inventive blood flow measuring apparatus it is possible to carry out for the first time the determination of the flow of blood through tissues according to the advantageous $H_2$ clearance measurement method or technique without a measuring current which is physiologically questionable for humans. This blood flow measuring apparatus is simple to use, operationally reliable and also can be operated by trained attendants or the like.

A major advantage of the present invention resides in the fact that with this blood flow measuring apparatus there can be undertaken a potential difference measurement under physiologically non-problematic conditions. In particular, the inventive blood flow measuring apparatus also enables accomplishing measurements with small quantities of hydrogen and in regions which normally are only accessible through the blood vessels, such as, for example, at the region of the heart. This preferred embodiment is manifested by its pronounced security for humans and its great measuring sensitivity.

In particular, the tissue only partially serves as a galvanic element. The current flowing through the tissue is negligible and especially does not generate any secondary effects due to ion displacement which would impair the measurement.

A further aspect of the present invention is concerned with a substantially needle-shaped measuring probe for use with a blood flow measuring apparatus operating according to the $H_2$ clearance measurement technique, comprising a measuring electrode, a reference electrode and a neutral electrode mounted in the substantially needle-shaped measuring probe, and a measuring channel cable with which there is releasably connected the substantially needle-shaped measuring probe.

BRIEF DESCRIPTION OF THE DRAWINGS

The invention will be better understood and objects other than those set forth above, will become apparent when consideration is given to the following detailed description thereof. Such description makes reference to the annexed drawings wherein:

FIG. 3 is a circuit diagram of a preferred embodiment of a blood flow measuring apparatus according to the present invention; and FIGS. 4a, 4b and 4c are respective fragmentary front views of different constructions of measuring probe.

DETAILED DESCRIPTION OF THE PREFERRED EMBODIMENTS

Describing now the drawings, it is to be understood that only enough of the construction of the blood flow measuring apparatus has been depicted therein, in order to simplify the illustration, as needed for those skilled in the art to readily understand the underlying principles and concepts of the present invention.

Figure 1:
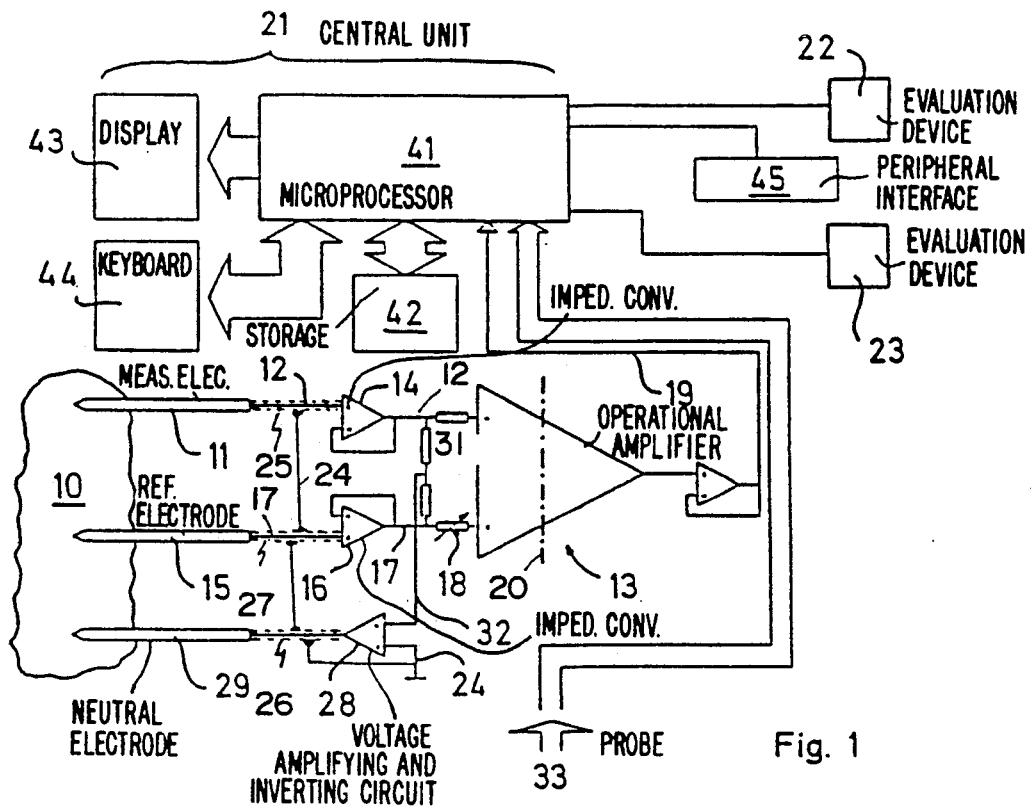
FIG. 1 is a circuit diagram of a simple embodiment of a blood flow measuring apparatus according to the present invention.

Turning attention now to the drawings, the circuit diagram depicted in FIG. 1 illustrates a measuring electrode 11 which is implanted in a tissue 10 at which measurements are to be performed. This measuring electrode 11 is connected by an input line or conductor 12 with a first input of a current and voltage isolated differential amplifier 13. This current and voltage isolated differential amplifier 13 forms a potential separated interface or galvanic separation 20 between a data acquisition section and a display and evaluation section of the measuring apparatus. According to a preferred embodiment, the measuring electrode 11 comprises a platinum electrode and the potential signal of this measuring electrode 11 is transmitted by means of an impedance converter circuit or impedance converter 14.

A reference electrode 15 implanted in the tissue 10 is connected by an input line or conductor 17 with a second input of the current and voltage isolated differential amplifier 13 and, in the preferred embodiment, comprises a silver electrode or a silver-containing electrode, especially an AgCl-electrode. In order to minimize the current which flows with such galvanic elements, the metals of these electrodes is selected such that their natural or inherent chemical potentials E° lie close to one another. In the preferred embodiment, in particular the signal of the reference electrode 15 is delivered by means of an impedance converter 16 and for the null balance by means of a regulatable or variable resistor 18. This null balance is important in order to compensate local changes in the temperature of the tissue, the pH-value or other effects which impair the measurement values, for example, ion transport with ionphorese or medication applications.

The output of the current and voltage isolated differential amplifier 13 is connected by a signal line or conductor 19 with a central unit 21 which digitizes the measurement signals by means of a suitable and thus not here illustrated analog-digital converter. This central unit 21 additionally comprises suitable means, for example, a storage programmable control and, in particular, standardized interfaces, in order to, for instance, connect and control different evaluation devices 22 and 23 so as to provide, for instance, a real time representation of a voltage-time diagram.

Such interfaces enable electronic linking with other instruments like, for instance, an infusomat, a perfusor, a respirator, or general patient monitoring devices, such as oxygen-, pH-, blood pressure- and respiratory frequency monitoring.

It should be understood that the output of the current and voltage isolated differential amplifier 13 can be directly connected with a data recorder or additional computers can be connected with the central unit 21 for evaluation of the measurement data.

What is important as concerns the safety of humans for the inventive blood flow measuring apparatus are the high-ohm constructed inputs of the impedance converters 14, 16 and the current and voltage isolated differential amplifier 13 which, in the preferred embodiment, limit the short-circuit current to less than 32 pA. A suitable current and voltage isolated differential amplifier 13 is the commercially available isolation amplifier sold under the commercial designation Burr-Braun ® 3656, as such described in greater detail in the July 1984 Product Data Manual of Burr-Braun Corporation, located at International Airport Industrial Park, P.O. Box 1140, Tucson, Ariz. More specifically, this special electronic module possesses input resistances of $1 \cdot 10^{13}$ ohms and a voltage or potential isolation exceeding 3.5 kV.

In particular, in the preferred embodiments of the present invention, the impedance converters 14 and 16 arranged forwardly or at the input side of the differential amplifier 13, possess an input resistance of $10^{42}$ ohms. The differential amplifier 13 can be an integrated transformer-coupled isolation amplifier having an input resistance of at least $1 \cdot 10^{13}$ ohms.

The measuring sensitivity of the present blood flow measuring apparatus is appreciably increased by the shields or screens 25 and 27 provided for the input lines 12 and 17 of the measuring electrode 11 and the reference electrode 15, respectively.

The spurious voltages induced at these shields or screens 25 and 27 by external spurious fields are tapped-off by an input line or conductor 24 and delivered to the non-inverting or positive input of a voltage amplifying and inverting circuit 28, the output of which is connected with a neutral electrode 29. The inverting or negative input of this voltage amplifying and inverting circuit 28 is connected by an input line or conductor 32 with a voltage divider 31 for forming the average or mean value of the potential measured by the measuring electrode 11 and the reference electrode 15. Consequently, the neutral electrode 29 produces a potential which is opposite the external spurious field at the tissue to be examined and as an active driver electrode compensates this spurious potential. Moreover, the neutral electrode 29 is also shown provided with a shield or screen 26 likewise connected by the voltage amplifying and inverting circuit 28 with the neutral electrode 29.

Figure 2:
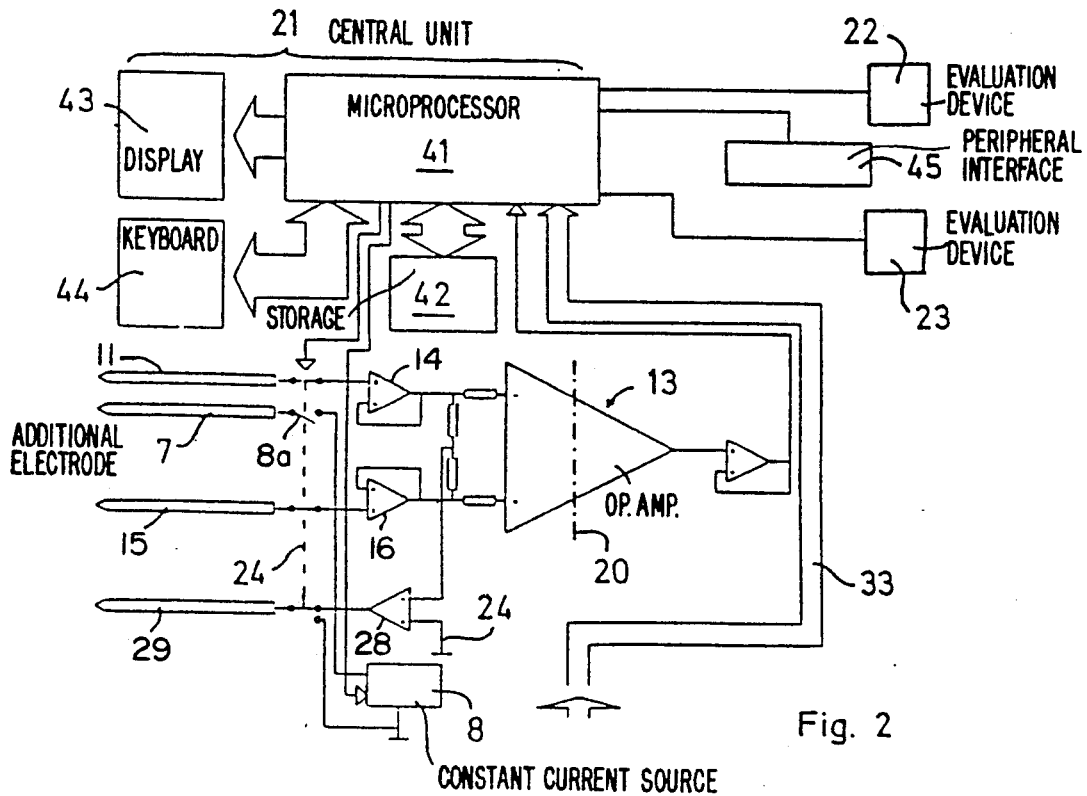
FIG. 2 is a circuit diagram of a modified embodiment of a blood flow measuring apparatus according to the present invention.

For the sake of completeness, it is here mentioned that such shields or screens 25, 26 and 27 only have been specifically shown in FIG. 1, but are equally provided in the arrangements of FIGS. 2 and 3, where for purposes of simplification of the drawings have been conveniently omitted from those drawing illustrations.

Further constructions of the inventive blood flow measuring apparatus will suggest themselves to those skilled in the art. Thus, for example, further probes 33 can be directly connected with the central unit 21 in order to improve the measurement values. In particular, it will be understood that there can be undertaken additional measurements of the tissue temperature, pH-values, $O_2$-partial pressure, $O_2$-content and so forth or there can be integrated in the circuit facilities for smoothing and filtering.

Equally, it is within the skill of those versed in the art to use a multiplicity of measuring and reference electrodes and an appropriate evaluation circuit, in order to, for instance, display the measured data in three-dimensional representation.

Turning next to the modified embodiment of inventive blood flow measuring apparatus depicted in FIG. 3, a commercially available microchip 34 comprising a noise-free bipolar precision amplifier is used as operational amplifier. Such a microchip 34 which is suitable for purposes of the present invention is described, for example, in the article entitled "Datenerfassungs-Chip ersetzt 30 Standard-ICs" (roughly translated as: "Data Acquisition Chip Replaces 30 Standard Integrated Circuits"), of G. McGlinchey et al. appearing in the publication "Electronik", 13/22.6.90, pages 90 to 93. The galvanic isolation 20 between the data acquisition section and the evaluation section of the blood flow measuring apparatus, which is important for the present invention, in the embodiment under discussion is arranged behind or at the output side of the central unit 21, whereas this potential-separated interface 20 of the prior embodiment is located in front of or at the input side of the central unit 21 due to the use of a current and voltage isolated differential amplifier 13. In contrast to the first considered exemplary embodiment, here the output signals are conducted by an opto-bus 35 which affords in a natural manner the galvanic isolation.

A further development of the inventive blood flow measuring apparatus, depicted in both FIG. 2 and FIG. 3, relates to the use thereof for active electrolysis, in which there is actively locally increased the $H_2$-content of the tissue through which flows the blood, by means of an additional electrode 7, especially a platinum electrode. The advantage of this further development will be directly discernible. On the one hand, it is possible to produce, independent of inhalation, for example, with the aid of a $H_2$-spray, a sufficiently high hydrogen concentration in the region to be measured and, on the other hand, the electrolysis time and the electrolysis current can be beneficially employed as a measure of the hydrogen concentration. With this modified construction, the additional electrode 7 is connected by means of a switch 8a to a constant current source 8 which is designed to be able to deliver currents of 0 to 50 μA and connected with the microprocessor 41 of the central unit 21.

This central unit 21 additionally embodies a storage 42, a display module 43 and a keyboard 44. According to a tested embodiment, the individual measuring electrodes are grouped together into a measuring probe which is detachably coupled with a shielded or screened measuring channel cable, generally indicated by reference numeral 60 in FIG. 4a. The measuring probe 50 is of substantially needle-shape and possesses, as shown in FIGS. 4a, 4b and 4c, bevelled tips 55. In a simple construction, the measuring probe 50 comprises a hollow stainless steel needle 48 into which there are installed the silver electrode 46 and the platinum electrode 47. The hollow stainless steel needle 48 thus simultaneously serves as shield or screen and as probe support or carrier. It should be understood that suitable means or expedients are provided for mutually isolating and mounting the individual electrodes, especially by lacquer coating and casting resin.

FIG. 4b depicts a probe tip for use as active electrolysis probe. To this end, there is provided an additional electrode 7 which forms a geometrically exactly defined galvanic element with the other electrodes at the bevelled needle surface or tip 55. By means of the other electrodes it is possible to measure simultaneously or subsequent to this local electrolysis. It should be understood that the measuring probe is connected with the blood flow measuring apparatus by means of a releasable plug connection, for example, a bayonet joint or connection or a snap connection or the like, particularly since such measurements can be performed for observation over a longer period of time, and thus, the probe need not be newly positioned for each individual measurement. Also, it should be understood the inventive blood flow measuring apparatus can be equipped with a plurality of measuring circuits for a plurality of measuring probes. The evaluation devices 22 and 23 used for the evaluation of the read measuring values are connected to appropriate peripheral interfaces 45. The present blood flow measuring apparatus in particular contains analog outputs for an XY-plotter or recorder, digital displays and measuring indicator display lights.

The methods used in the software for the evaluation of the measurement signals are predicated upon principles which set forth the change of the gas concentration as a function of the blood flow. The person skilled in the art is well aware of publications relevant in this regard as well as other mathematical evaluation methods, for example, as disclosed in the publication "Stroke", Volume 13, No. 3, 1982, pages 347 to 355, the article "Measurement of rCBF by $H_2$ Clearance: Theoretical Analysis of Diffusion Effects", authored by Robert A. Pierce et al, to which reference may be readily had and the disclosure of which is incorporated in its entirety by reference.

Amplifications of the blood flow measuring apparatus, for example, through the use of a PC-monitor, devices for protection of the blood flow measuring apparatus, probe mounts, all constitute subject matter well within the expertise of those skilled in the art. Equally, the materials used for the probes can be suitably selected, in particular, the electrode supports or carriers can be fabricated from suitably selected plastic materials.

It is also obvious for the person skilled in this technology to employ the present blood flow measuring apparatus for blood flow measurements where there is not inhaled, produced or injected hydrogen, rather where there are administered ascorbic acids, that is, vitamin C or other redox substances, as such are known from indicator dilution technique. The algorithms suitable for the evaluation of this measuring method are well known to those versed in this field, as exemplified in the aforementioned publication "Stroke", Volume 13, No. 3, 1982, pages 347 to 355.

The blood flow measuring apparatuses heretofore described can be beneficially employed for every organ through which flows blood or through which flows or is flushed by another body liquid. These blood flow measuring apparatuses are deemed to be particularly suitable for cardiovascular time measurements, shunt measurements, heart volume measurements, liquor circulation measurements, infusion volume measurements, vessel throughflow volume measurements, diffusion volume- and concentration measurements, urine elimination measurements, lacrimal fluid measurements, in transplantation and implantation surgery, plastic surgery, tumor surgery, neuro surgery, radio therapy, paradonology, endodontry, during the workings of medications and dosing thereof, human and animal physiology, for assessing the effects of acupuncture, and many other fields of application.

It should be understood that the inventive blood flow measuring apparatuses not only be can used for diagnostic and therapy progress control in the medical field, but also in industrial applications, such as for the measurement of the gas concentration of certain gases, like $CO_2$ or $O_2$ in a heated fluid.

While there are shown and described present preferred embodiments of the invention, it is distinctly to be understood the invention is not limited thereto, but may be otherwise variously embodied and practiced within the scope of the following claims.

What is claimed is:

1. A blood flow measuring apparatus operating according to the $H_2$ clearance measurement technique, comprising:

a measuring electrode having an input line;

a reference electrode having an input line;

a neutral electrode having an input line;

an operational amplifier having inputs;

a signal display device operatively connected with the operational amplifier;

each said measuring electrode and said reference electrode are formed of metals whose natural chemical potential lie close to one another;

means for connecting the measuring electrode and the reference electrode to the inputs of the operational amplifier in order to form the difference of the potentials of the measuring electrode and the reference electrode;

a respective shield provided for the input line of each of the measuring electrode, the reference electrode and the neutral electrode to safeguard against external spurious fields;

a voltage amplifying and inverting circuit having a noninverting input and an inverting input;

the shields of at least the measuring electrode and the reference electrode and the input lines of the measuring electrode and the reference electrode are connected by the non-inverting input of the voltage amplifying and inverting circuit with the neutral electrode in order to produce a potential in tissue of a patient which is opposite to inductive or capacitive coupled-in potential fluctuations;

a voltage divider connected between the input lines of the measuring electrode and the reference electrode;

the inverting input of the voltage amplifying and inverting circuit being connected with the voltage divider in order to form an average value of he potentials of the measuring electrode and reference electrode;

a connectable electrolysis electrode;

a constant current source provided for the connectable electrolysis electrode; and means for selectively connecting the constant current source with the neutral electrode for selectively connecting the connectable electrolysis electrode with the constant current source.

2. The blood flow measuring apparatus according to claim 1, wherein:
the operational amplifier comprises a current and voltage isolated differential amplifier having high-ohm inputs.

3. The blood flow measuring apparatus according to claim 2, wherein:
the current and voltage isolated differential amplifier comprises an integrated transformer coupled isolated amplifier having an input resistance of at least 1 10—ohms.

4. The blood flow measuring apparatus according to claim 1, further including:
means for evaluating operatively connected with the operational amplifier;
the operational amplifier comprises a microchip having a substantially noise-free bipolar precision amplifier; and
an opto-bus provided for the galvanic isolation between the microchip and the evaluation means.

5. The blood flow measuring apparatus according to claim 1, further including:
a substantially needle-shaped measuring probe in which there are mounted the measuring electrode, the reference electrode and the neutral electrode; and
a measuring channel cable with which there is releasably connected the substantially needle-shaped measuring probe.

6. The blood flow measuring apparatus according to claim 5, further including:
a second measuring electrode having an input line;
a second reference electrode having an input line;
a second neutral electrode having an input line;
a second operational amplifier having an input line;
said signal display device being operatively connected with the second operational amplifier;
each said second measuring electrode and said second reference electrode are formed of metals whose natural chemical potential lie close to one another;
means for connecting the second measuring electrode and the second reference electrode to the inputs of the operational amplifier in order to form the difference of the potentials of the second measuring electrode and the second reference electrode;
a respective shield provided for the input line of each of the second measuring electrode, the second reference electrode and the second neutral electrode to safeguard against external spurious fields;
a second voltage amplifying and inverting circuit having a non-inverting input and an inverting input;
the shields of at least the second measuring electrode and the second reference electrode and the input lines of the second measuring electrode and the second reference electrode are connected by the non-inverting input of the second voltage amplifying and inverting circuit with the second neutral electrode in order to produce a potential in tissue of the patient which is opposite to inductive or capacitive coupled-in potential fluctuations;

a second voltage divider connected between the input lines of the second measuring electrode and the second reference electrode;
the inverting input of the second voltage amplifying and inverting circuit being connected with the second voltage divider in order to form an average value of the potentials of the second measuring electrode and the second reference electrode;
a substantially needle-shaped additional probe in which there are mounted the second measuring electrode, the second reference electrode and the second neutral electrode; and
a second measuring channel cable with which there is releasable connected the substantially needle-shaped additional probe.

7. A blood flow measuring apparatus operating according to the $H_2$ clearance measurement technique, comprising:
a measuring electrode having an input line;
a reference electrode having an input line;
a neutral electrode having an input line;
an operational amplifier having inputs;
each said measuring electrode and said reference electrode are formed of metals whose natural chemical potential lie close to one another;
means for connecting the measuring electrode and the reference electrode to the inputs of the operational amplifier in order to form the difference of the potentials of the measuring electrode and the reference electrode;
a respective shield provided for the input line of each of the measuring electrode, the reference electrode and the neutral electrode to safeguard against external spurious fields;
a voltage amplifying and inverting circuit having a noninverting input and an inverting input;
the shields of at least the measuring electrode and the reference electrode and the input lines of the measuring electrode and the reference electrode are connected by the non-inverting input of the voltage amplifying and inverting circuit with the neutral electrode in order to produce a potential in tissue of a patient which is opposite to inductive or capacitive coupled-in potential fluctuations;
a voltage divider connected between the input lines of the measuring electrode and the reference electrode;
the inverting input of the voltage amplifying and inverting circuit being connected with the voltage divider in order to form an average value of the potentials of the measuring electrode and reference electrode;
a connectable electrolysis electrode;
a constant current source provided for the connectable electrolysis electrode; and
means for selectively connecting the connectable electrolysis electrode with the constant current source.

8. The blood flow measuring apparatus according to claim 7, further including:
a substantially needle-shaped measuring probe in which there are mounted the measuring electrode, the reference electrode and the neutral electrode; and
a measuring channel cable with which there is releasably connected the substantially needle-shaped measuring probe.

* * * * *